United States Patent
Ma et al.

(10) Patent No.: US 10,633,574 B2
(45) Date of Patent: Apr. 28, 2020

(54) COMPOSITIONS AND METHODS TO RECOVER IRREDUCIBLE WATER FOR ENHANCED FORMATION EVALUATION

(71) Applicant: Saudi Arabian Oil Company, Dhahran (SA)

(72) Inventors: Shouxiang Mark Ma, Dhahran (SA); Nedhal Musharfi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 36 days.

(21) Appl. No.: 15/667,021

(22) Filed: Aug. 2, 2017

(65) Prior Publication Data

US 2019/0040303 A1 Feb. 7, 2019

(51) Int. Cl.
*C09K 8/584* (2006.01)
*G01N 33/24* (2006.01)
*C09K 8/035* (2006.01)
*E21B 43/16* (2006.01)
*E21B 49/08* (2006.01)

(52) U.S. Cl.
CPC ............... *C09K 8/584* (2013.01); *C09K 8/035* (2013.01); *E21B 43/16* (2013.01); *E21B 49/08* (2013.01); *G01N 33/246* (2013.01)

(58) Field of Classification Search
CPC ....................................................... E21B 43/16
USPC ..................................................... 166/250.01
See application file for complete search history.

(56) References Cited

U.S. PATENT DOCUMENTS

| | | | |
|---|---|---|---|
| 2,345,935 A | 4/1944 | Hassler | |
| 2,679,159 A | 5/1954 | Messer | |
| 4,530,400 A * | 7/1985 | Hsieh | C09K 8/584 166/270.1 |
| 5,048,328 A | 9/1991 | Puri | |
| 5,146,086 A | 9/1992 | De et al. | |
| 5,328,440 A | 7/1994 | Chen et al. | |
| 5,563,333 A | 10/1996 | Haines et al. | |
| 5,783,760 A | 7/1998 | Haines et al. | |
| 5,969,240 A | 10/1999 | Eadington et al. | |
| 6,021,662 A | 2/2000 | Moulu et al. | |
| 7,072,809 B2 | 7/2006 | Egermann et al. | |
| 7,363,164 B2 | 4/2008 | Little et al. | |
| 7,917,294 B2 | 3/2011 | Coope et al. | |
| 8,768,628 B2 | 7/2014 | Ghedan et al. | |

(Continued)

FOREIGN PATENT DOCUMENTS

| | | |
|---|---|---|
| CN | 103278418 A | 9/2013 |
| CN | 104990854 A | 10/2015 |

(Continued)

OTHER PUBLICATIONS

Falode et al., Wettability Effects on Capillary Pressure, Relative Permeability, and Irreducible Saturation Using Porous Slate; 2014; Journal of Petroleum Engineering.

(Continued)

*Primary Examiner* — Taras P Bemko
(74) *Attorney, Agent, or Firm* — Bracewell LLP; Constance G. Rhebergen; Brian H. Tompkins (57) ABSTRACT

Provided here are compositions and improved methods for recovering portion of irreducible water saturation in a porous rock sample. Compositions used here contain a displacement fluid and a surfactant, and lead to an increased recovery of the irreducible water from the porous rock sample.

20 Claims, 7 Drawing Sheets

(56) References Cited

U.S. PATENT DOCUMENTS

| | | |
|---|---|---|
| 2011/0306525 A1 | 12/2011 | Lighthelm |
| 2013/0081822 A1* | 4/2013 | Han .............. C09K 8/588 166/369 |
| 2014/0305649 A1 | 10/2014 | Tang et al. |
| 2015/0111716 A1 | 4/2015 | Hakimuddin |
| 2015/0198036 A1 | 7/2015 | Kleinberg et al. |
| 2016/0024372 A1 | 1/2016 | Fathi Najafabadi |

FOREIGN PATENT DOCUMENTS

| | | |
|---|---|---|
| CN | 204903529 U | 12/2015 |
| EP | 2341372 A1 | 7/2011 |
| EP | 3006538 A1 | 4/2016 |
| WO | 2010092095 A1 | 8/2010 |

OTHER PUBLICATIONS

Izadi et al., A New Approach in Permeability and Hydraulic-Flow-Unit Determination; Aug. 2013; SPE; pp. 257-264.

Ma, et al., Resolving Mixed Salinity Challenges with a Pulsed Neutron Methodology; Journal of Petroleum Technology; Aug. 2015; pp. 87-89.

Mandal A. et al., Surfactant Stabilized Nanoemulsion: Characterization and Application in Enhanced Oil Recovery; 2012; International Scholarly and Scientific Research & Innovation, 6(7):pp. 537-542.

Mosayeb, et al., The Effect of Non-Ionic Surfactants on the Interfacial Tension Between Crude Oil and Water; Petroleum & Coal, 2012; vol. 54(2); pp. 110-113.

Muherei, M.A. et al., Effect of Electrolyte on Synergism of Anionic-Nonionic Surfactant Mixture; 2007; 7(10): pp. 1362-1371.

Xiao et al., Calculation of Irreducible Water Saturation (S(wirr)) from NMR Logs in Tight Gas Sands; Sep. 4, 2013.

Xu et al., The Impact of Irreducible Water on Stress-Sensitivity of Gas Reservoir Rocks; 2013; Applied Mechanics and Materials; 2013; vols. 246-247, pp. 472-475.

International Search Report and Written Opinion for related PCT application PCT/US2018/044727 dated Nov. 15, 2018.

\* cited by examiner

COMPOSITIONS AND METHODS TO RECOVER IRREDUCIBLE WATER FOR ENHANCED FORMATION EVALUATION

FIELD

This disclosure relates to compositions and methods generally directed to recovery of irreducible water from core samples for evaluation of a hydrocarbon reservoir.

BACKGROUND

Hydrocarbon recovery factor is defined as the ratio of producible hydrocarbon to in situ hydrocarbon, namely the original hydrocarbon in place. Determining the amount of in situ hydrocarbon is key to the economic assessment of hydrocarbon production at a particular location, and also dictates the production methods to be utilized there. One of the attributes of characterizing the reservoir quality and hydrocarbon quantity is irreducible water saturation (Swir); the water saturation resulting from the balance between capillary pressure that holds on to the water and gravitational force that drains the water downward. For good quality rock, the value of irreducible water saturation is usually very low if it is high above the free water level, but still can be reduced lower if the rock with the irreducible water could be moved higher from its original place, i.e., by increasing gravitational driving forces. Thus, "irreducible" water saturation can, theoretically, be reduced if the balance between the draining force and binding force is disrupted, by either increasing gravitational draining force or reducing capillary binding force. For core samples taken from an oil column in a reservoir with oil-based coring fluid, the water saturation measured from a core sample with good rock quality is usually very low, depending on the type of rock and the location of the core sample with respect to the free water level. This very low water saturation is referred to as irreducible water saturation in this disclosure. In terms of water property, this irreducible water is most likely connate water, water trapped in the pores space during formation of the rock. Another source is interstitial water (Swi), which is generally defined as water that occurs naturally within the rock pore space. Part of this irreducible water saturation may be recovered by using centrifuge or core-flood techniques. These techniques involve flowing oil or gas through a preserved native state core samples taken from the oil column, or spinning it in a centrifuge to displace the water with oil or gas. These techniques often result in recovery of some of the water, but the core samples are often destructed, depending on their mechanical strength, and thus, the success rate is low. It is very challenging and expensive to obtain consistent results.

SUMMARY

Several disadvantages were recognized by the inventors and various embodiments of this disclosure were developed to address these shortcomings in the art. Certain embodiments disclosed and described here include compositions containing a displacement fluid and a surfactant. Displacement fluids used here include fluids that are less dense than water. Certain embodiments include a method of recovering portion of irreducible water saturation in a porous rock sample. An embodiment of the method includes the steps of providing a composition containing a displacement fluid and a surfactant to a porous rock sample with an irreducible water saturation to produce a treated rock sample; and subjecting the treated rock sample to centrifugation to extract a portion of irreducible water. The porous rock sample can be a rock representative of a hydrocarbon reservoir. The centrifugation can be carried out under conditions that preserve physical integrity of the porous rock sample. In some embodiments, the displacement fluid is less dense than water. The displacement fluid can be diesel, toluene, dodecane, or combinations thereof. The displacement fluid can be other functionally similar fluids. The surfactant can be an organic surfactant. The composition can contain diesel as the displacement fluid and an organic surfactant. The organic surfactant in certain embodiments can be at least 0.01 wt % of the composition containing diesel and the organic surfactant. The organic surfactant in certain embodiments can be about 0.5 wt % of the composition containing diesel and the organic surfactant. The organic surfactant in certain embodiments can be about 1 wt % of the composition containing diesel and the organic surfactant.

Certain embodiments include methods of enhanced recovery of irreducible water from a porous rock sample. One such method includes the steps of mixing a displacement fluid and a surfactant to produce a composition; allowing the composition to interact with a porous rock sample with an irreducible water saturation to produce a treated rock sample; and subjecting the treated rock sample to centrifugation under conditions to preserve physical integrity of the porous rock sample and to obtain an amount of irreducible water from the treated rock sample greater amount of irreducible water obtained from the porous rock sample w without treatment with the composition. The porous rock sample can be a rock representative of a hydrocarbon reservoir. The centrifugation can be carried out under conditions that preserve physical integrity of the porous rock sample. In some embodiments, the displacement fluid is less dense than water. The displacement fluid can be diesel, toluene, dodecane, or combinations thereof. The displacement fluid can be other functionally similar fluids. The surfactant can be an organic surfactant. The composition can contain diesel as the displacement fluid and an organic surfactant. The organic surfactant in certain embodiments can be at least 0.01 wt % of the composition containing diesel and the organic surfactant. The organic surfactant in certain embodiments can be about 0.5 wt % of the composition containing diesel and the organic surfactant. The organic surfactant in certain embodiments can be about 1 wt % of the composition containing diesel and the organic surfactant. The irreducible water recovered from the treated rock sample can be subject to geochemical analysis. The irreducible water recovered from the treated rock sample can be subject to water salinity analysis.

Certain embodiments include methods of measuring irreducible water saturation in a porous rock sample. One such method includes the steps of providing a composition containing diesel and an organic surfactant to a porous rock sample with an irreducible water saturation to produce a treated rock sample; subjecting the treated rock sample to centrifugation to extract an amount of irreducible water; and determining the irreducible water saturation of the porous rock sample responsive to the amount of irreducible water obtained from the treated rock sample. The porous rock sample can be a rock representative of a hydrocarbon reservoir. The centrifugation can be carried out under conditions that preserve physical integrity of the porous rock sample.

Numerous other aspects, features and benefits of the present disclosure may be made apparent from the following detailed description taken together with the drawing figures. The systems can include less components, more components, or different components depending on desired analysis goals.

BRIEF DESCRIPTION OF THE DRAWINGS

While this disclosure is susceptible to various modifications and alternative forms, specific embodiments are shown by way of example in the drawings and will be described in detail here. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

In the following description, numerous specific details are set forth in order to provide a thorough understanding of the various embodiments. In other instances, well-known processes and methods may not be described in particular detail in order not to unnecessarily obscure the embodiments described here. Additionally, illustrations of embodiments here may omit certain features or details in order to not obscure the embodiments described here.

In the following detailed description, reference is made to the accompanying drawings that form a part of the specification. Other embodiments may be utilized, and logical changes may be made without departing from the scope of the disclosure. Therefore, the following detailed description is not to be taken in a limiting sense.

The description may use the phrases "in some embodiments," "in various embodiments," "in certain embodiment," or "in embodiments," which may each refer to one or more of the same or different embodiments. Furthermore, the terms "comprising," "including," "having," and the like, as used with respect to embodiments of the present disclosure, are synonymous.

Fluid saturation in a reservoir evolves as fluid flow in and out of the system. For example, oil saturation decreases with oil production and subsequent replacement of oil by another fluid such as water that enters the reservoir during waterflooding. This entry of new fluids can be either naturally or artificially by water or gas injection. The saturations of the different fluids in a reservoir are, therefore, measured periodically by periodically running appropriate reservoir surveil lance logs and analyzing the logs for water saturation changes. Porosity is the capacity of a rock to hold fluids, so saturation for any particular fluid, which is the ratio of fluid volume to pore space volume, is the fraction of the porosity that holds such fluid. Hydrocarbon saturation is one minus the water saturation. There is usually a film of water covering the surface of the pores.

Rupturing of this water film by polar components of crude oil changes reservoir rock wettability.

Formation water trapped in a dry oil or gas producing zone of porosity ($\phi$) is bound by capillary forces. If the amount of capillary bound water ($V_{wir}$) in an unit of rock bulk volume is normalized with respect to porosity $\phi$, the porosity normalized $V_{wir}$ is then called "irreducible" water saturation ($S_{wir}=V_{wir}/\phi$). There is another perspective that irreducible water saturation can be reduced if an applied external pressure P is high enough so that the pressure difference ($\Delta P$) across interface is greater than the capillary binding pressure ($P_c$). Part of capillary bound water can be recovered if $\Delta P > Pc$.

Knowing the properties of capillary bound connate water, such as formation water salinity (FSAL) is important for formation evaluation since FSAL is an input parameter for log interpretation (such as resistivity log) and environmental correction (such as neutron log) and geological studies such as depositional environmental studies, diagenesis, and basin modeling.

Recovery of a sample of the capillary bound water from the hydrocarbon zone is difficult as the volume of water can be small and the capillary pressure $P_c$ can be high. The industry's best practice is to mount the core plug, in its reservoir native state, inside a centrifuge core holder. The core holder also contains another fluid that displaces the fluids from the core sample until the two fluids reach equilibrium at the set centrifuge speed. The core holder is spun at a RPM (revolution per minute) high enough such that the applied centrifugal force ($\Delta P$) is greater than the capillary pressure. The original water that is displaced from the core sample is measured and an average water saturation value for the core sample is determined. This technique has been shown to recover some of the water, but the core samples can often be destructed, depending on their mechanical strength, and thus, the success rate is low. In addition, only a few specialized core analysis laboratories are able to produce consistent results. So there is a need for an easier and more robust method to recover a portion of the irreducible water without destruction of the core sample.

Embodiments disclosed here involve methods of reducing the capillary-bound trapped water for the purpose of recovering part of irreducible water at a reduced applied pressure, so that more water can be recovered for geo-chemical analysis for applications in engineering and geoscience, without mechanically damaging the core sample. Embodiments disclosed here involve methods of recovering a portion of irreducible water saturation in a porous rock sample. One such method includes the steps of: providing a composition containing a displacement fluid and a surfactant to a porous rock sample with an irreducible water saturation to produce a treated rock sample; subjecting the treated rock sample to centrifugation under conditions to preserve physical integrity of the porous rock sample and to extract an amount of irreducible water. The amount of irreducible water obtained from the treated rock sample is greater than amount of irreducible water obtained from the porous rock sample without treatment with the composition containing a displacement fluid and a surfactant. The porous rock sample is a rock representative of a hydrocarbon reservoir. The centrifugation can be carried out under conditions that preserve physical integrity of the porous rock sample. The displacement fluid is less dense than water. In certain embodiments, the displacement fluid is one or more of mineral oil, diesel, toluene, or dodecane. In certain embodiments, the surfactant is one or more of an ionic surfactant, a nonionic surfactant, or an organic surfactant. In an embodiment, the composition contains diesel and an organic surfactant.

Embodiments disclosed here also include methods of enhanced recovery of irreducible water from a porous rock sample. One such method includes the steps of: mixing a displacement fluid and a surfactant to produce a composition; allowing the composition to interact with a porous rock sample of an irreducible water saturation with the composition to produce a treated rock sample; and subjecting the treated rock sample to centrifugation under conditions to preserve physical integrity of the porous rock sample and to extract an amount of irreducible water greater than amount of irreducible water obtained from the porous rock sample without treatment with the composition. The porous rock sample is a rock representative of a hydrocarbon reservoir. In certain embodiments, the displacement fluid is one or more of mineral oil, diesel, toluene, or dodecane. In certain embodiments, the surfactant is one or more of an ionic surfactant, a nonionic surfactant, or an organic surfactant. In an embodiment, the composition contains diesel and an organic surfactant. The organic surfactant can be at least 0.01 wt % of the composition containing diesel and the organic surfactant. The organic surfactant can be about 0.05 wt % of the composition containing diesel and the organic surfactant. The organic surfactant can be about 1 wt % of the composition containing diesel and the organic surfactant.

Embodiments include compositions containing a displacement fluid and a surfactant. These composition can also contain particles that reduce interfacial tension between irreducible water and the displacement fluid. Displacement fluids that can be used in embodiments here include mineral oil, dodecane, isoparaffin (such as Soltrol® 130), and diesel. These fluids are less dense than water and immiscible with water. Example of surfactants that can be used include nonionic surfactants such as Triton X-100, biosurfactants, or organic surfactants. Examples of organic surfactants can be oxidized fatty acids, organic alcohols, amines, amides, ethers, ketones, organic sulphonates, and combinations thereof. The organic surfactant can be a mixture, such as VERSACOAT® organic surfactant that is available as a commercial product from M-I SWACO, a Schlumberger company, headquartered in Houston, Tex. A formulation of the VERSACOAT® organic surfactant contains 60-100 wt % tall oil reaction product, 10-30 wt % hydrotreated light petroleum distillates, and 5-10 wt % methyl alcohol. The lower the density of the displacement fluid, the larger the fluid density difference, the larger will be the driving force as per Eq. 3. Surfactants chosen to operate in these compositions are soluble in the displacement fluid and reduce interfacial tension between the displacement fluid and the irreducible water. Certain surfactants can also act as a dispersant agent to minimize water in oil emulsion. The concentration of the surfactant used in combination with the displacement fluid can range from 0.001 to 5 wt % of the composition. In various embodiment, the concentration of the surfactant used in combination with the displacement fluid can range from 0.005 wt % to 0.5 wt % of the composition, or from 0.005 wt % to 0.01 wt %, or from 0.01 wt % to 0.05 wt %, or from 0.01 wt % to 0.5 wt %, or from 0.01 wt % to 0.1 wt %, or from 0.5 wt % to 1 wt %, or from 0.01 wt % to 1 wt %, or from 0.01 wt % to 5 wt % of the composition. In certain embodiments, the composition contains refined mineral oil and a surfactant. In certain embodiments, the composition contains diesel and VERSACOAT®. Addition of the surfactant reduces the interfacial tension between the displacement fluid and the irreducible water. In certain embodiments, there is at least a four-fold reduction in the interfacial tension between the displacement fluid and the irreducible water. Thus, the capillary force is also reduced at least about four-fold, and more irreducible water is recovered.

In certain embodiments, the amount of surfactant used in combination with the displacement fluid is the minimum amount required to reduce oil-water interfacial tension to a desired low value. The surfactant is added to the displacement fluid and mixed before the displacement fluid is in contact with the core sample. If the core sample is taken from an oil zone, crude oil in the core sample will be miscible with the displacing refined mineral oil-surfactant composition, then the effective displacing fluid will be the mixture between the crude oil and the refined mineral oil. Crude oil may need to be displaced miscibly by the displacing fluid in a conventional core flood set up before centrifuge to ensure contact between the displacing fluid with surfactant and irreducible water. If core sample is taken from a gas zone, gas will be replaced with refined mineral oil inside the core sample during the test. Conventionally using emulsion breaker, then centrifuge the fluid mixture to separate the two liquids.

The various embodiments disclosed here relate to methods to reduce the capillary force-bound irreducible water in a core sample in order to improve recovery of the irreducible water. Recovered irreducible water may be tested for geochemical analysis such as salinity to provide formation water salinity, which is an important parameter to properly evaluate and interpret borehole logs, such as a resistivity log or a neutron log.

Non-miscible fluids such as water and oil are considered to be in equilibrium in a subterranean reservoir. Capillary pressure is due to the curvature of the interface separating the two fluids and the interfacial tension. Capillary pressure $P_c$ is a product of interface curvature C and interfacial tension $\sigma$, as defined below:

$$Pc = C\sigma \qquad \text{(Equation 1)}$$

In porous media, C is a function of pore structure and wettability. To extract pore size distribution from capillary pressure measurement, pore bodies and pore throats in porous media are often modeled using cylindrical pore geometry model. Assuming r is the radius of a cylindrical pore and θ is the contact angle determined at the three phase contact (the wetting phase, the non-wetting phase, and the tube surface), then capillary pressure is determined as follows $$Pc = 2\sigma \cos \theta / r \qquad \text{(Equation 2)}$$

Capillary-bound water $S_{wir}$ is the water retained in pores and throats smaller than radius r at a specific capillary pressure Pc. So, as long as ΔP is greater than Pc, additional water can be recovered.

The three common ways to measure capillary pressure curves are mercury injection methods, porous plate methods, and centrifuge methods. Each one of these methods has its unique applications and limitations. Centrifuge methods are the only techniques in the industry that can be used to recover capillary-bound reservoir water.

In centrifuge test, centrifugal driving force is $$\Delta P = a\Delta\rho N^2(R-L/2)L \qquad \text{(Equation 3)}$$

Δρ is fluid density difference, N is centrifuge speed in rpm (revolutions per minute), R is distance from center of centrifuge to the outlet end of the core, L is core length, a is constant. For ΔP>Pc, the current industry practice is to increase ΔP by increasing the centrifuge speed N, for example.

Embodiments disclosed herein include methods to decrease Pc to a reduced value of Pc* by reducing fluid interfacial tension σ by adding an effective amount of surfactant to a displacement fluid, typically refined mineral oil. Further, to ensure the sample's mechanical integrity, the applied pressure differential should always be less than the rock sample's critical shear strength, $C_0$. Therefore, $C_0$>ΔP>Pc* becomes the operative condition in certain embodiments.

In order to determine reservoir irreducible water properties, three techniques are been used in the industry to recover irreducible water, or part of it.

The Dean-Stark distillation extraction method is a technique that enables the determination of water saturation in a core sample by solvent vaporization and condensation process. Oil and water are extracted by dripping a solvent, usually toluene or a mixture of acetone and chloroform, over the core samples. By heating the system, the in-situ water vaporizes, condenses in the condenser tube and is collected in a graduated receiver. The vaporized solvent also condenses, soaks the sample, and extracts the oil, which falls into the solvent flask. The experiment continues until the extracted solvent displays its original color. Water recovered by this technique is distilled water, not representative of formation water.

The second technique is a downhole estimation by running a pulsed neutron salinity log. This newly developed technique requires a minimum amount of salt volume, i.e., it will lose its sensitivity if water is too fresh, water saturation is too low, and porosity is too low.

The third technique is centrifuging the core sample at a very high speed (up to 16,000 RPM), to force part of the irreducible water out of the core sample. This technique is challenging, because little water is produced if rock is too tight and rock samples can be mechanically damaged if the applied pressure is too high. Embodiments disclosed herein improve the centrifuge technique. Methods currently in practice include preparing a native state core sample with initial water saturation, $S_{wir}$, and treating it with a displacing fluid. The core sample, treated with a displacement fluid, is then subject to centrifugation at a high speed to recover part of the irreducible water.

Figure 1:
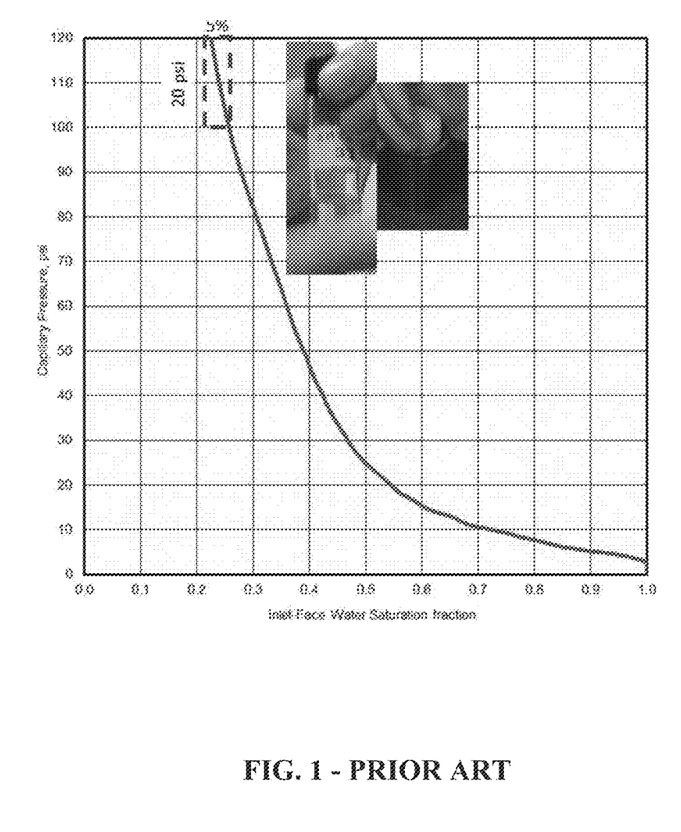
FIG. 1 is a graphical representation of the capillary pressure versus the amount of irreducible water extracted from a core sample of porosity of 0.084, using currently used practice in the industry by increasing drainage pressure from 100 to 120 psi.

To increase the extraction of the irreducible water using the centrifuge technique, current practice is to increase the centrifuge speed N, thus increasing the applied centrifugal force as per Equation 3 to ensure ΔP>Pc is satisfied. A finite additional volume of water may be produced. FIG. 1 is a graphical representation of the capillary pressure versus the amount of irreducible water extracted from a core sample of porosity of 0.084, using currently used practice in the industry. In this example, a finite change in displacing centrifugal pressure of about 20 psi, at an assumed reservoir capillary pressure of 100 psi (a function of free water level), can recover an additional 5% water saturation.

Figure 2:
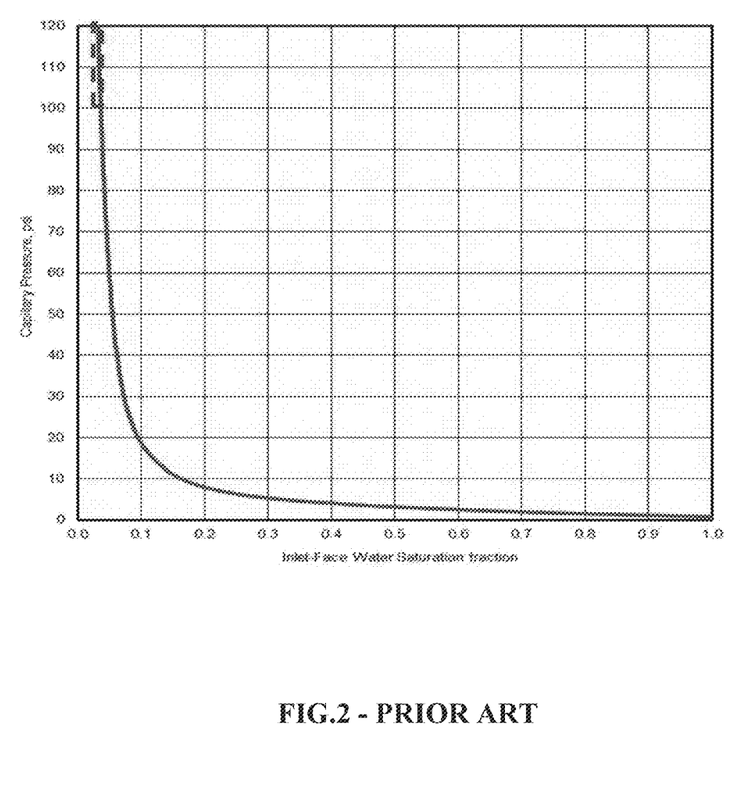
FIG. 2 is a graphical representation of the capillary pressure versus the amount of irreducible water extracted from a core sample of porosity of 0.164-0.167, using currently used practice in the industry by increasing drainage pressure from 100 to 120 psi.

For very good quality rocks, the irreducible water may be too low that the produced water may be too small to be measured. FIG. 2 is a graphical representation of the capillary pressure versus the amount of irreducible water extracted from a core sample of porosity of 0.164-0.167, using currently used practice in the industry. Here, a 20 psi change in centrifugal pressure yielded no measurable water. Increasing applied pressure to this very good quality rock sample with low initial water saturation, at an assumed reservoir capillary pressure of 100 psi (a function of free water level) had negligible effect.

In another example involving very low quality and tight rock samples, no capillary-bound water could be produced. The capillary-bound pressure may be so high that the condition ΔP>Pc is difficult to satisfy with a centrifuge. To satisfy the condition ΔP>Pc, the applied centrifugal force is higher than the rock's critical shear strength $C_0$ that is responsible to hold the rock fabric together. Under these conditions where ΔP>$C_0$, the applied high centrifugal force can crush the sample, thus causing permanent mechanical damage. Rock samples may be crushed if applied centrifugal force is higher than rock critical shear strength.

Water produced by displacement of the surfactant fluid in centrifuge may exist as emulsions. In certain embodiments, when water is separated from the produced fluid, a demulsifier or emulsion breaker can be selected and used to break the emulsion. Centrifuging the produced fluid sample may also be needed to further separate water out. Embodiments described here include methods to recover part of the irreducible water without the application of high centrifugal forces. Achieving the condition $C_0$>ΔP>Pc* provides several advantages over current industry practices. These methods allow recovery of part of the irreducible water in very low quality and tight rock samples. They also allow the recovery of the irreducible water in less cemented rock samples without mechanically crushing the sample. Certain embodiments include methods of measuring irreducible water saturation in a porous rock sample. A porous rock sample with an irreducible water saturation is contacted with a composition containing diesel and an organic surfactant to produce a treated rock sample. This treated rock sample is subject to centrifugation to extract an amount of irreducible water and the irreducible water saturation of the porous rock sample is determined in response to the amount of irreducible water obtained from the treated rock sample. The centrifugation can be carried out under conditions that preserve physical integrity of the porous rock sample.

Figure 3:
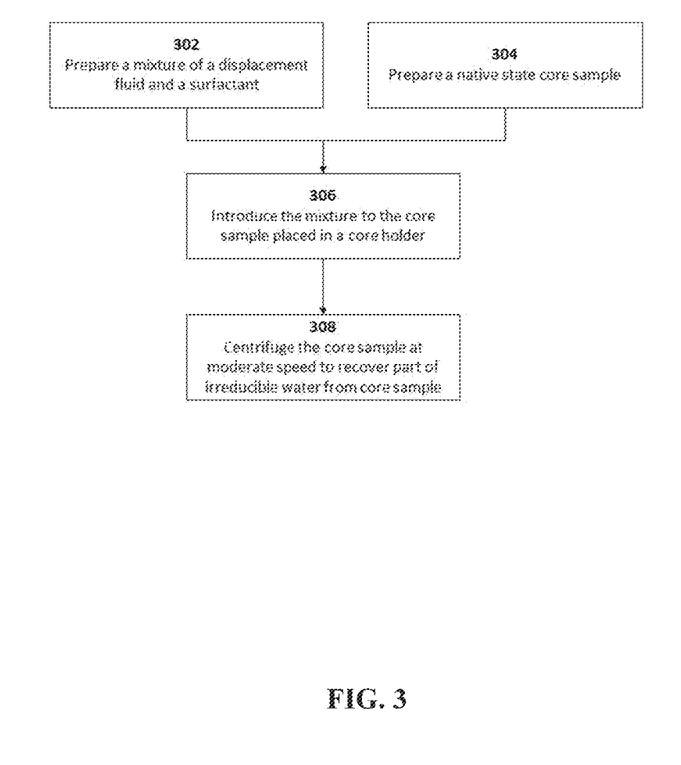
FIG. 3 is a block diagram of a method, according to an embodiment.

FIG. 3 is a block diagram of an improved method to recover part of capillary-bound irreducible water, according to an embodiment. This method includes the step 302 of preparing a composition containing a displacement fluid and a surfactant that reduces interfacial tension between the displacement fluid and the irreducible water. In step 304, a native state core sample with irreducible water saturation, $S_{wir}$, is prepared. Subsequently in step 306, the core sample is treated with the composition containing the displacement fluid and the surfactant, and in step 308, the treated core sample is subjected to centrifugation at a moderate speed to recover part of the irreducible water. This moderate speed can be more than ten times less than the maximum 16000 RPM applied when conventional method was used. For example, if a particular composition containing a displacement fluid and a surfactant decreases the interfacial tension by four times, then to attain the same pressure effects, the centrifugal speed or RPM can be reduced by at least sixteen times. Embodiments include using these methods for reservoir description, geological studies, and reservoir management. Using a composition containing a displacement fluid and a surfactant facilitates the recovery of capillary-bound water from core samples without mechanically damaging the core samples. Embodiments include using these methods in the petroleum industry, and also in applications in other industries that have a need to remove capillary bound water, such as porous media drying (bricks, cloths, etc).

Example 1

Figure 4:
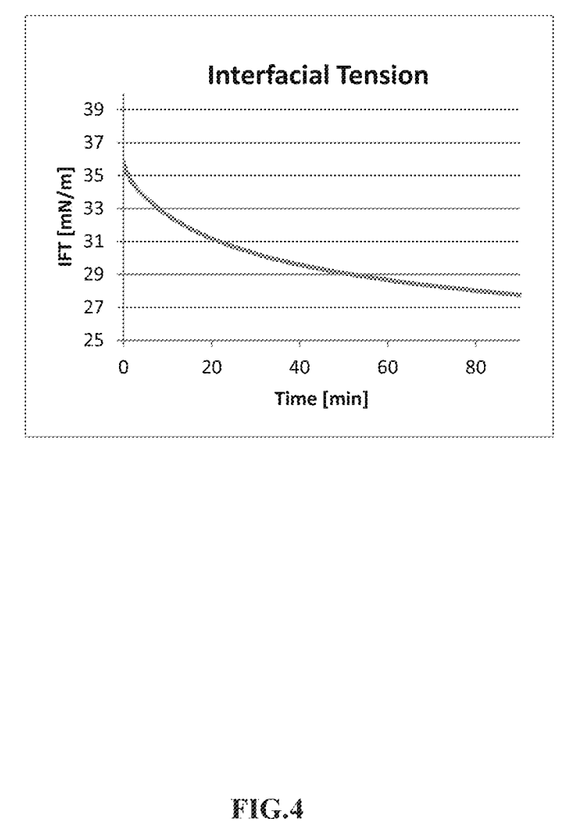
FIG. 4 is a graphical representation of the changes in the interfacial tension observed with respect to time using the diesel-surfactant composition, according to an embodiment.

In this example, a Ramé-hart tensiometer is employed to measure both contact angle as well as surface tension and interfacial tension. The pendant drop method, which is particularly well adapted to liquid-liquid interfaces, is based on the deformation of a drop. The shape of the drop depends on the balance between the gravity forces, which tend to elongate the drop, and the interfacial tension, which minimizes the surface of the interface and tends to make the drop spherical. Two pumps are connected to a cell, where the first one is used for the drop phase and the second one for the bulk phase. The fluids used in this example are deionized, degassed water for the drop phase and diesel or a diesel-surfactant composition for the bulk phase. An imaging system is used to capture the shape of the drop. A drop was suspended into a bulk fluid phase, comprising diesel and de-ionized water, from the end of the capillary injector, while keeping a constant pressure and temperature. The image of the drop profile was captured for further analysis. The droplet sizes ranged from about 2-20 μL, at a temperature of 30° C. FIG. 4 is a graphical representation of the changes in the interfacial tension observed with respect to time using the diesel-surfactant composition, according to an embodiment. The initial surface tension after the drop is formed decreases as the large molecules adsorb (collect) at the interface and reduce the surface tension.

Example 2

Figure 5:
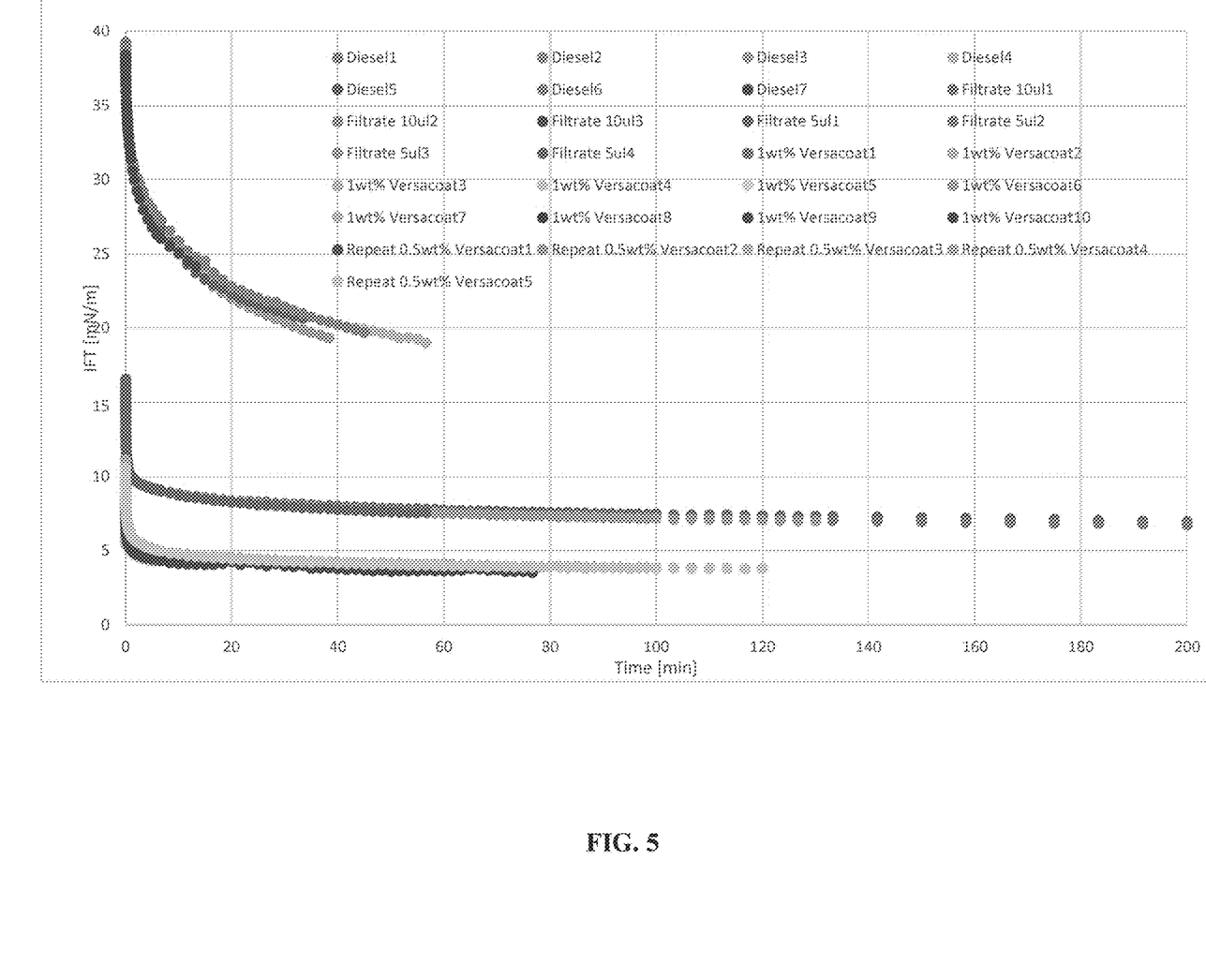
FIG. 5 is a graphical representation of the changes in the interfacial tension observed with respect to time using several diesel compositions and then several diesel-surfactant compositions at two different concentrations, according to an embodiment.

Experiments were conducted to study the effect of surfactants on the interfacial tension of several compositions containing diesel alone and others with diesel and an appropriate amount of surfactant, such as 0.5 wt % or 1 wt %. Standard oil-based muds containing the VERSACOAT® surfactant were also used to evaluate the comparative performance of the compositions discussed here, as these oil-based muds are used as drilling fluids and affect $S_{wir}$ observed from shallow logs. Interestingly, there was a significant decrease in the interfacial tension by using diesel-surfactant compositions, which correlates to importance of these compositions to recover irreducible water. A series of samples were prepared using the several diesel compositions and a surfactant at two different concentrations—at 1 wt % and at 0.5 wt %. About 10 mL of diesel was mixed at about 30° C. with appropriate amount of surfactant to arrive at the 1 wt % and at the 0.5 wt %. The surfactant used in the diesel-surfactant compositions here was the VERSACOAT® surfactant. The surfactant reduced the interfacial tension between the diesel and water by at least four to five times, and using 0.5 wt % of surfactant was as effective as using 1 wt % of the surfactant in the various diesel-surfactant compositions. FIG. 5 is a graphical representation of the changes in the interfacial tension observed with respect to time using several diesel compositions and then several diesel-surfactant compositions at two different concentrations, according to an embodiment.

Example 3

Figure 6:
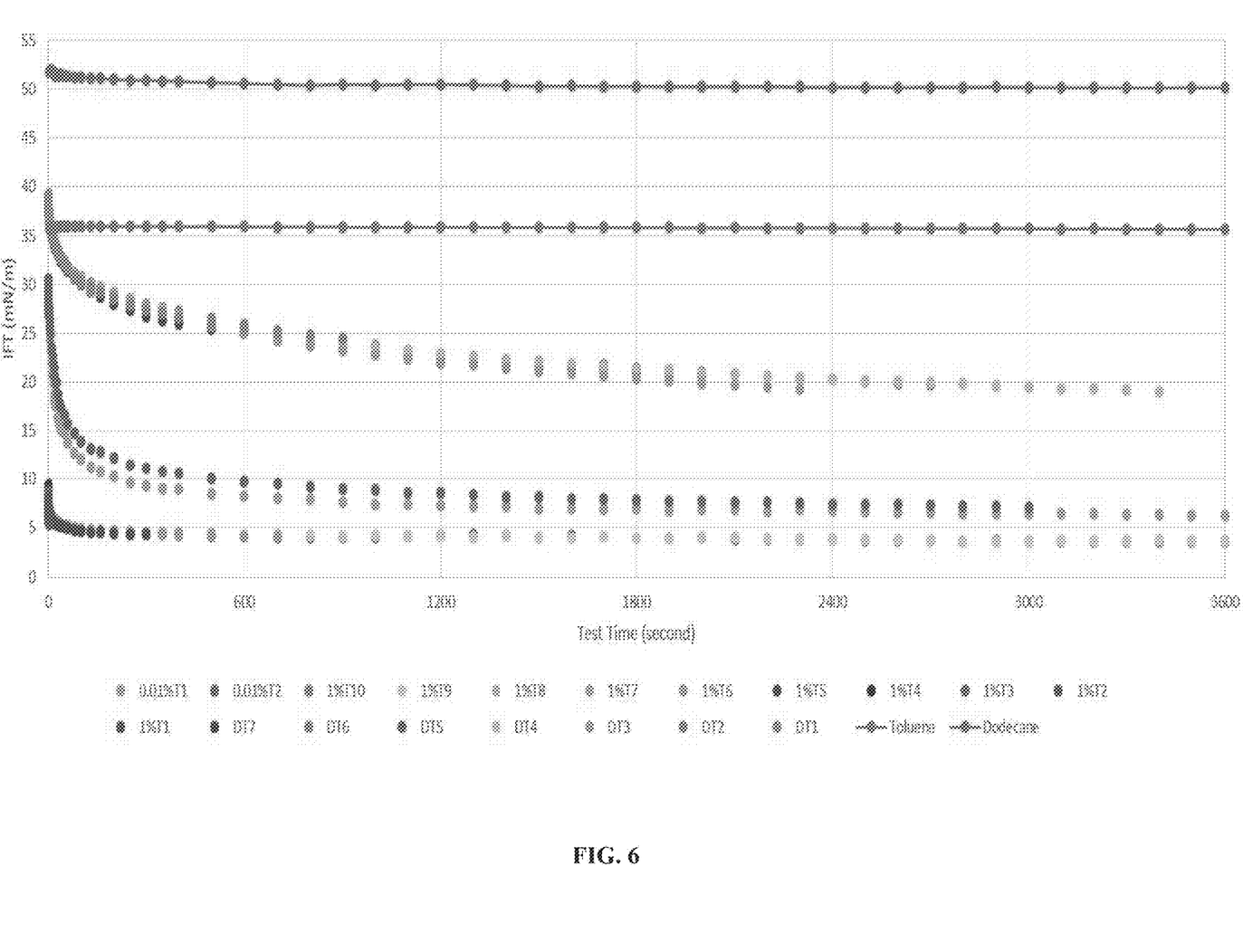
FIG. 6 is a graphical representation of the interfacial tension observed with respect to time using several diesel, toluene, and dodecane compositions and then several diesel-surfactant compositions at two different concentrations, according to an embodiment.

Experiments were conducted to study the effect of surfactants on the interfacial tension of several diesel, toluene, and dodecane compositions. A series of samples were prepared using the several diesel compositions and a surfactant at two different concentrations—at 1 wt % and at 0.01 wt %. The surfactant used in the diesel-surfactant compositions here was the VERSACOAT® surfactant. The surfactant reduced the interfacial tension between the diesel and water by at least four to five times, and using 0.01 wt % of surfactant was less effective than using 1 wt % of the surfactant in the various diesel-surfactant compositions. FIG. 6 is a graphical representation of the interfacial tension observed with respect to time using several diesel, toluene, and dodecane compositions and then several diesel-surfactant compositions at two different concentrations, according to an embodiment. The interfacial tension was reduced by almost six times or higher, which can lead to extraction of an increased amount of irreducible water.

Example 4

Experiments were conducted to study the effects of the diesel-surfactant composition on the recovery of the irreducible water from core samples. Core samples in FIGS. 1 and 2 were from a gas reservoir, while core samples used in this experiment was from an oil reservoir. Tests were repeated with the same core sample—first with a diesel composition and then repeated with a diesel-surfactant composition. About 10 mL of diesel was mixed at room temperature with appropriate amount of surfactant to arrive at the 0.5 wt % VERSACOAT® containing composition. The core holder were spun at RPMs corresponding to different pressures as indicated on FIG. 7. The core sample has a porosity of 0.2446 and a permeability of 592 millidarcy.

Figure 7:
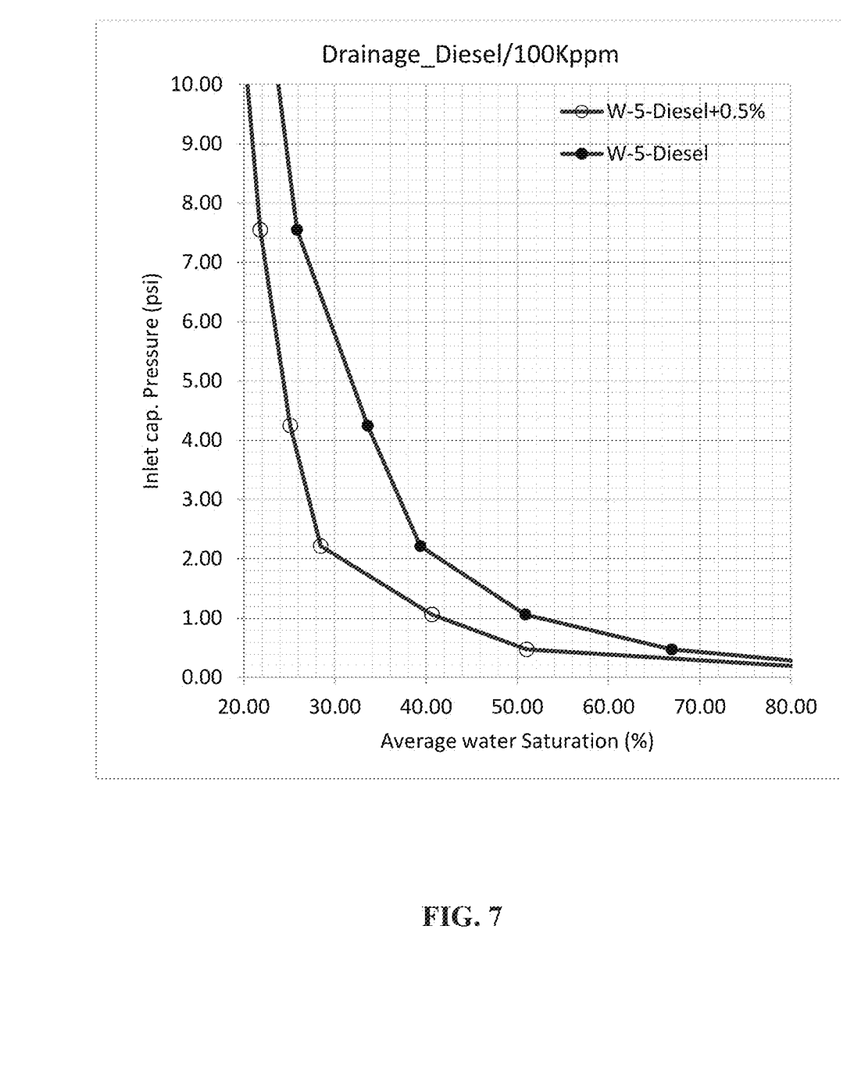
FIG. 7 is a graphical plot of the changes in capillary pressure versus the average water saturation from a core sample using a diesel composition and a diesel-surfactant composition, according to an embodiment.

The irreducible water that is displaced from the core samples was measured and an average saturation value for the core samples was determined at the end of the test after the remaining of the $S_{wir}$ was recovered by method such as Dean-Stark. FIG. 7 is a graphical representation of the capillary pressure versus the average water saturation from core samples using a diesel composition and a diesel-surfactant composition, according to an embodiment. Diesel by itself displaces about 100 kppm (kilo parts per million) of water. When the composition containing diesel and 0.5 wt % of the surfactant was used, more water was recovered consistently at different pressures (or RPMs). About 4% more irreducible water was obtained at 10 psi. More water was recovered consistently at different pressures (or RPMs).

Ranges may be expressed herein as from about one particular value and to about another particular value. When such a range is expressed, it is to be understood that another embodiment is from the one particular value and/or to the other particular value, along with all combinations within said range. Where the range of values is described or referenced herein, the interval encompasses each intervening value between the upper limit and the lower limit as well as the upper limit and the lower limit and includes smaller ranges of the interval subject to any specific exclusion provided.

Where a method comprising two or more defined steps is recited or referenced herein, the defined steps can be carried out in any order or simultaneously except where the context excludes that possibility. Further modifications and alternative embodiments of various aspects of the compositions and methods disclosed here will be apparent to those skilled in the art in view of this description. Accordingly, this description is to be construed as illustrative only and is for the purpose of teaching those skilled in the art the general manner of carrying out the embodiments. Elements and materials may be substituted for those illustrated and described here, parts and processes may be reversed or omitted, and certain features of the embodiments may be utilized independently, all as would be apparent to one skilled in the art after having the benefit of this description of the embodiments.

Various modifications to these embodiments will be readily apparent to those skilled in the art, and changes may be made in the elements described here without departing from the spirit and scope of the embodiments as described in the following claims.

What is claimed is:

1. A method of recovering portion of irreducible water saturation in a porous rock sample, comprising the steps of:
   providing a composition containing a displacement fluid and a surfactant to a porous rock sample with an irreducible water saturation to produce a treated rock sample, wherein the displacement fluid is less dense than water and immiscible with water, and the surfactant reduces interfacial tension between the displacement fluid and the irreducible water, wherein the surfactant is soluble in the displacement fluid; and
   subjecting the treated rock sample to centrifugation to extract a portion of irreducible water.

2. The method of claim 1, wherein the porous rock sample is a rock representative of a hydrocarbon reservoir.

3. The method of claim 1, wherein the centrifugation is under conditions to preserve physical integrity of the porous rock sample.

4. The method of claim 1, wherein the displacement fluid is diesel.

5. The method of claim 1, wherein the displacement fluid is toluene.

6. The method of claim 1, wherein the displacement fluid is dodecane.

7. The method of claim 1, wherein the surfactant is an organic surfactant.

8. The method of claim 1, wherein the composition contains diesel and an organic surfactant.

9. The method of claim 8, wherein the organic surfactant is at least 0.5 wt % of the composition containing diesel and the organic surfactant.

10. The method of claim 1, wherein the composition further comprises a plurality of nanoparticles.

11. A method of enhanced recovery of irreducible water from a porous rock sample, comprising the steps of:
   mixing a displacement fluid and a surfactant to produce a composition, wherein the displacement fluid is less dense than water and immiscible with water, wherein the surfactant is soluble in the displacement fluid;
   allowing the composition to interact with a porous rock sample with an irreducible water saturation to produce a treated rock sample, wherein the surfactant reduces interfacial tension between the displacement fluid and the irreducible water; and
   subjecting the treated rock sample to centrifugation under conditions that preserve physical integrity of the porous rock sample to obtain an amount of irreducible water from the treated rock sample greater than amount of irreducible water obtained from the porous rock sample without treatment with the composition.

12. The method of claim 11, wherein the porous rock sample is a rock representative of a hydrocarbon reservoir.

13. The method of claim 11, wherein the displacement fluid is diesel.

14. The method of claim 11, wherein the surfactant is an organic surfactant.

15. The method of claim 11, wherein the composition contains diesel and an organic surfactant.

16. The method of claim 15, wherein the organic surfactant is at least 0.01 wt % of the composition containing diesel and the organic surfactant.

17. The method of claim 15, wherein the organic surfactant is about 0.05 wt % of the composition containing diesel and the organic surfactant.

18. The method of claim 15, wherein the organic surfactant is about 0.5 wt % of the composition containing diesel and the organic surfactant.

19. The method of claim 11, wherein the irreducible water recovered from the treated rock sample is subject to geochemical analysis.

20. The method of claim 11, wherein the irreducible water recovered from the treated rock sample is subject to water salinity analysis.

* * * * *